United States Patent [19]
Malen et al.

[11] 3,988,464
[45] Oct. 26, 1976

[54] CYCLOPROPYLAMINES AS PHARMACEUTICALS

[75] Inventors: Charles Malen, Fresnes; Monique Desnos, Issy les Moulineaux; Michel Laubie, Vaucresson; Jean-Claude Poignant, Bures S/Yvette, all of France

[73] Assignee: Science Union et Cie. Societe Francaise de Rechereche Medical, Suresnes, France

[22] Filed: Dec. 26, 1973

[21] Appl. No.: 427,999

[30] Foreign Application Priority Data
Dec. 28, 1972 United Kingdom............... 59886/72

[52] U.S. Cl.............................. 424/272; 260/307 R
[51] Int. Cl.²...................... A01N 9/22; A01N 9/28
[58] Field of Search.................. 424/272; 260/367 R

[56] References Cited
UNITED STATES PATENTS
3,626,067  12/1971  Harvey.............................. 424/272

OTHER PUBLICATIONS
Chem. Abst. 59, 7533(f)(1963)–"N–Substituted—2–aminooxazolines".
Chem. Abst. 71 101842(x)(1969)–"2(cycloalkylamino)–2–oxazolines" Hiltmann et al.
Chem. Abst. 65 13681(e)(1966)–"Synthesis of –oxazolinyl-2-amines-isothiocyanates"–Pfeil et al.

Primary Examiner—James O. Thomas, Jr.
Assistant Examiner—D. W. Robinson
Attorney, Agent, or Firm—Gordon W. Hueschen

[57] ABSTRACT

The present invention relates to cyclopropylmethyl amines substituted by a heterocyclic radical.

More particularly the heterocyclic radical is a nitrogen containing ring with 5, 6 or 7 links interrupted by another hetero atom selected from the group consisting of oxygen, sulphur and imino—NH—

The invention also relates to the acid addition salts thereof with physiologically compatible mineral or organic acids.

The invention extends to the processes for making them and the intermediates produced hereto.

The invention also includes the pharmaceutical compositions incorporating as active ingredient at least one compound of the invention with an inert carrier.

The compounds have therapeutic utility namely on the cardio-vascular diseases and on the neuro-psychological disturbances.

10 Claims, No Drawings

CYCLOPROPYLAMINES AS PHARMACEUTICALS

DESCRIPTION OF THE PRIOR ART

The prior art is illustrated with the publication of Corrodi [Helv. Chim. Acta 46 (1963) 1059] and U.S. Pat. No. 3,626,067; French Pat. Nos. 1,576,097 and 1,485,790; French Drug Pat. No. 2,382 M.

SUMMARY OF THE INVENTION

The present invention relates to substituted cyclopropylmethylamines of the general formula I:

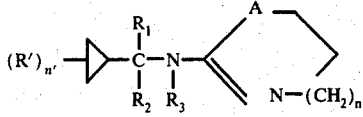

wherein $R_1$ and $R_2$ which are the same or different, each represents a hydrogen atom, a lower alkyl radical, an unsubstituted cyclopropyl radical or a cyclopropyl radical bearing one or more lower alkyl radicals $R'$ represents a hydrogen atom or a lower alkyl radical $R_3$ represents a hydrogen atom or a lower alkyl radical A represents an oxygen atom, a sulphur atom or an imino —NH— radical $n$ represents 0, 1 or 2 and $n'$ represents 0, 1, 2 or 3 and their physiologically compatible acid addition salts.

The invention relates to processes for making the same and to pharmaceutical compositions.

PREFERRED EMBODIMENTS

The present invention provides a substituted cyclopropylmethylamine of the general formula I:

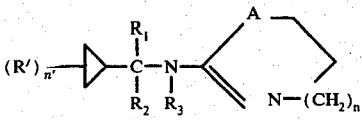

wherein $R_1$ and $R_2$, which are the same or different, each represents a hydrogen atom, a lower alkyl radical, an unsubstituted cyclopropyl radical or a cyclopropyl radical bearing one or more lower alkyl radicals $R'$ represents a hydrogen atom or a lower alkyl radical $R_3$ represents a hydrogen atom or a lower alkyl radical A represents an oxygen atom, a sulphur atom or an imino —NH— radical $n$ represents 0, 1 or 2 and $n'$ represents 0, 1, 2 or 3.

The present invention also provides an acid addition salt of this compound with a mineral or organic acid.

The term "lower alkyl" is used herein to designate an alkyl radical having from 1 to 6 carbon atoms.

When $R_1$ and $R_2$ are different, the carbon atom which bears these substituents is asymetric and thus the compound may be resolved into its optical antipodes.

The resolution may be carried out by reacting the compound of general formula I with an optically active acid, for example, d-camphosulphonic acid, d-camphoric acid, l-methylacetic acid, d-ketogulonic acid, d-dibenzoyl-tartaric acid or d-tartramic acid.

The resulting optically active salt is transformed into the optically active base by adding a strong mineral or organic base, or a strong mineral acid.

The resolution may be also effected at another step either by using a previously resolved starting material II or by resolving the intermediate ureas IV.

Compounds of the general formula I wherein the heterocyclic radical is oxazoline (A = oxygen, $n = 0$), thiazoline (A = sulphur, $n = 0$), imidazoline (A = imino, $n = 0$), thiazine (A = sulphur, $n = 1$), dihydro meta-oxazine (A = oxygen, $n = 1$), tetrahydro 1,3-diazepine (A = imino, $n = 2$), tetrahydro 1,3-oxepine (A = oxygen, $n = 2$) are particularly useful.

The present invention also provides as presently preferred compounds the cyclopropylmethylamines of the formula I'

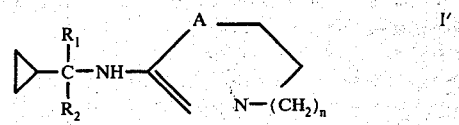

wherein $R_1$ and $R_2$, which are the same or different, each represents a hydrogen atom, a lower alkyl radical or a cyclopropyl radical;

A represents an oxygen atom, a sulphur atom or an imino —NH— radical;

and $n$ represents 0, 1 or 2.

The compounds of the present invention have useful pharmacological and therapeutical properties. In particular, they influence the cardiovascular system. They possess, moreover, a depressant action on the central nervous system, which may result in hypnosis, analgesic action and/or antipsychotic effects. The compounds of the invention are used principally as anti-hypertensive drugs.

The present invention also provides a pharmaceutical preparation comprising as active ingredient at least one compound of general formula I, in admixture or conjunction with a pharmaceutically suitable carrier. The invention further provides a pack or system comprising at least one compound of the general formula I together with instructions, the instructions requiring the administration of the compound (s) to a subject to relieve hypertension.

The pharmaceutical preparation may be in any form suitable for oral, parenteral, sublingual, percutaneous or rectal administration. More particularly, it may be in the form of tablets, coated tablets, gelules, ampules, phials, multidose phials, capsules, syrups, drops, sublingual tablets, lotions, solutions or suppositories.

The usual dosage may vary depending of the theraputical use, the age of the patient and the way of administration.

It may range from 1.5 mg to 5 mg per dosage unit. The daily dosage may range from 1.5 mg to 30 mg. The preferred unit dosage ranges from 2 to 4 mg.

The pharmaceutical compositions including as active ingredient one or more compounds of general formula I are prepared according to methods known in the pharmaceutical technology.

The invention also provides a process for the preparation of a compound of general formula I which comprises condensing a cyclopropylamine of general formula II:

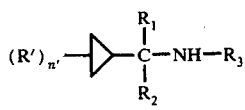    II wherein R', $R_1$, $R_2$, $R_3$ and $n'$ are defined as above; either (a) with a ω-halogeno alkyl iso-cyanate or -thiocyanate having the general formula III:

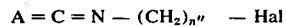    III wherein
A is an oxygen or sulphur atom,
Hal is a chlorine or bromine atom
and $n''$ is an integer of from 2 to 4
to form a disubstituted urea or thiourea of general formula IV:

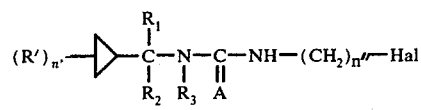    IV wherein the substituents R', $R_1$, $R_2$, $R_3$, A, $n'$, $n''$ and Hal are defined as previously stated, which is cyclised by heating into a compound of general formula I:

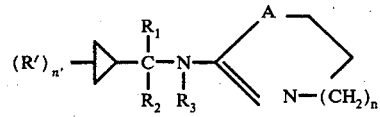    I wherein
A is an oxygen or sulphur atom,
$n$ is 0, 1 or 2 and
R', $R_1$ and $R_2$ are defined as previously stated, and, if desired, salifying this compound by adding a mineral or organic acid, or resolving it by means of an optically active acid, or, (b) with a cyclic S-methyl isothiourea of the formula V:

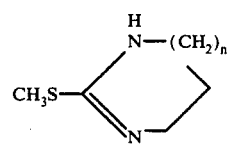    V wherein
$n$ is 0, 1 or 2
to form a compound of general formula I:

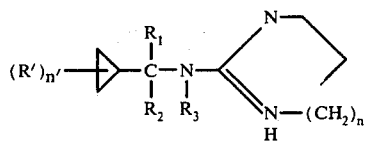    I wherein $R_1$, $R_2$ and $n$ are defined as above, and, if desired, salifying this compound by adding a mineral or organic acid.

The condensation between a cyclopropylamine of general formula II with an isocyanate or isothiocyanate of general formula III is preferably carried out in an inert solvent, for example, a cyclic or non cyclic ether, a trialkylamine, an aromatic hydrocarbon, a lower alkyl alkanoate, or a cycloalkane.

The most preferred solvents are isopropyl ether or tetrahydrofuran as an ether, triethylamine as a trialkylamine; xylene, toluene or benzene as an aromatic hydrocarbon; ethyl acetate as a lower alkyl alkanoate; cyclopentane or cyclohexane as a cycloalkane, or a mixture of two or more thereof.

The cyclisation of the thio-urea or urea of general formula IV occurs by heating, preferably in an aqueous medium. This dehydrohalogenation may be effected in the presence or in absence of a basic agent in order to bind any hydrohalic acid formed during the cyclisation. The basic agent may be a mineral basic agent, for example, an alkali metal carbonate or bicarbonate, an alkali metal hydroxide, an alkaline-earth oxide or carbonate, magnesia, or a basic salt of aluminium. It may be also an organic agent, for example, a dialkyl amine, a trialkylamine, dimethyl-aniline or pyridine.

The cyclisation is preferably effected by warming at a temperature of from 50° to 120° C, depending of the nature of the solvent and of the molecule to be dehydrohalogenated. Preferably, this operation is effected at about 100° C.

The condensation between the cyclopropylamine of general formula II and a cyclic S-methyl isothiourea of formula V occurs preferably by heating from 50° to 150° C in a polar solvent. Examples of suitable polar solvents are dimethylformamide, dimethyl acetamide, dimethyl sulphoxide, hexaphosphorotriamide and divinylsulphone.

The present invention also provides another process for producing compounds of general formula I for which A represents an oxygen atom, i.e. compounds having the formula

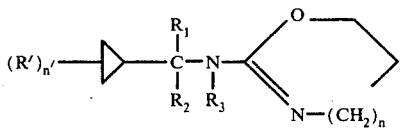    I in which the definition of the substituents are the same as above which consists in submitting a cyclopropylamine of general formula II

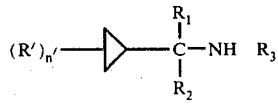    II wherein the substituents $R'_1$, $R_1$, $R_2$, $R_3$ and $n'$ are defined as above with an aryl halogeno formate of the formula

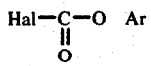

wherein
Hal is fluorine or chlorine and
Ar is a phenyl radical or a radical substituted by one or more radicals of electrophilic character in order to produce a carbamate of the formula VI

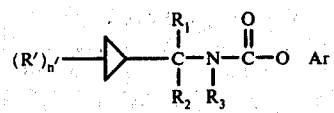

wherein $R'_1$, $R_1$, $R_2$, $R_3$, Ar and $n'$ are defined as above given, condensing the carbamate of formula VI with an aminoalkanol of formula VII

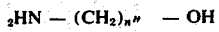

wherein $n''$ is an integer from 2 to 4 to get a hydroxyalkyl urea of formula VIII

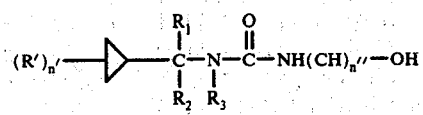

wherein the definitions of the substituents remain unchanged submitting the hydroalkyl urea of formula VIII to the action of an halogenating agent to form the corresponding ω-halogenoalkyl urea of formula IV

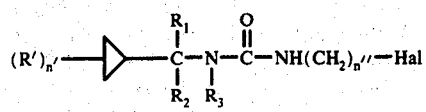

and cyclising the latter by warming to produce a compound of general formula I wherein A is an oxygen atom.

This process is also defined with the following features:
- the aryl halogenoformate is preferably a chloride
- the aryl radical is preferably a phenyl radical, a nitro phenyl radical, a dinitro phenyl radical or a chloro nitro phenyl radical
- the condensation with the aryl halogenoformate is carried out in the presence of a basic agent such a tri-lower alkylamine, a di-lower alkyl aniline, pyridine, collidine, 4-dimethylamino pyridine or dimethyl formamide,
- the reaction between the carbamate and the amino alkanol is performed in water or in mixture of water and a water-miscible solvent
- the chlorinating agent is thionyl chloride, phosphorus chloride, phosphorus bromide, phosphorus oxychloride or N-bromo acetamide.

The invention also provides as new compounds the intermediate compounds:

substituted cyclopropylamines of the formula

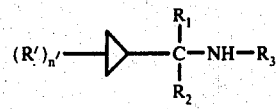

wherein $n'$, $R'$, $R_1$, $R_2$ and $R_3$ are defined as above, with the proviso that when $R'$ is hydrogen and $R_1$ is a cyclopropyl radical, $R_3$ is a lower alkyl radical
ureas and thio ureas of formula IV

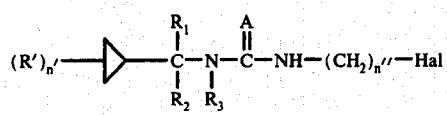

wherein
A is an oxygen or a sulphur atom and
$R'$, $R_1$, $R_2$, $R_3$, Hal, $n'$ and $n''$ are defined as previously cited and more particularly:
N-(dicyclopropylmethyl)N′-(β-chloroethyl) urea
N-(dicyclopropylmethyl)N′-(β-chloroethyl) thiourea
N-(1′-cyclopropylethyl)N′-(β-chloroethyl) urea
N-(dicyclopropylmethyl)N′-(β-chloropropyl) urea
N-(cyclopropylmethyl) N′-(β-chloroethyl) urea
N-hydroalkyl ureas of formula VIII

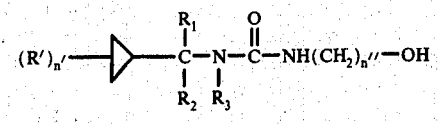

wherein the substituents $R'$, $R_1$, $R_2$, $R_3$, $n'$ and $n''$ are defined as above and namely N-(dicyclopropylmethyl) N′-(β-hydroxy ethyl) urea
carbamates of general formula VI

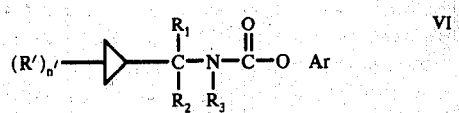

wherein the substituents R', $R_1$, $R_2$, $R_3$, Ar and n' are defined as above and namely phenyl dicyclopropylmethyl carbamate.

Most of the starting materials of general formula II are already described in the litterature [see U.S. Pat. No. 3,184,509 - Corrodi Helv. Chim. Acta 46 (1963) 1059 and Timberlake J. Org. Chem. 33 (1968) 4054 ].

The other starting materials may be prepared according to similar methods starting from a cyclopropyl ketone and condensing the latter with hydroxylamine, reducing the oxime thus produced with sodium and an alkanol or with a mixed alkali-metal hydride, recovering the cyclopropyl methylamine which may be alkylated by condensation with a lower alkyl aldehyde and reducing the Schiff base by means of an alkali-metal borohydride.

The isocyanates and thiocyanates of general formula IV may be prepared according to the process described by W. Sefken Annalen 562 (1949) 75.

The following examples illustrate the invention:

EXAMPLE 1

2-(dicyclopropylmethyl) oxazoline and its neutral fumarate

Step a. N-(dicyclopropylmethyl) N'-($\beta$-chloroethyl) urea

A solution made from 13.4 g of dicyclopropylmethylamine in 30 ml tetrahydrofuran is added dropwise to a solution of 13 g of $\beta$-chloroetyl isocyanate in 15 ml tetrahydrofuran while maintaining the inner temperature from 0° to +5° C. Then, the reaction mixture is kept at room temperature for 15 hours. Afterwards, the solution is evaporated to dryness and the dry residue, weighing 26.5 g, is used as such for the next step of the synthesis. For analytical purpose, a sample of the raw urea is recrystallised from acetonitrile. The N-(dicyclopropylmethyl) N-($\beta$-chloroethyl) urea occurs as white crystals melting at 103°–104° C with decomposition.

Step b. 2-(dicyclopropylmethylamino) oxazoline 25 g of raw urea obtained by step a) are suspended in 150 ml of water and heated under reflux for 2 hours. After allowing the temperature of the mixture to return to room temperature, the aqueous solution is extracted with ether. The aqueous phase is separated and made alkaline by adding concentrated ammonia.

The resulting precipitate is separated by suction, washed with water and dried. 11.8 g of 2-(dicyclopropylmethylamino) oxazoline are thus recovered, melting at 105°–106° C. A mixture of the latter with N-(dicyclopropylmethyl) N'-($\beta$-chloroethyl) urea gives a decrease of the melting point.

For analysis, the product is further purified by means of sublimation at 80° C under a pressure of 0.5 mm Hg. The purified product melts at 106°–107° C.

The elemental analysis, the IR and RMN spectra confirm the structure of the obtained product.

Step c. 2-(dicyclopropylmethylamino) oxazoline, neutral fumarate 12 g of 2-(dicyclopropylmethylamino) oxazoline obtained by step b) are dissolved in 60 ml ethanol. To this solution, a solution made from 3.8 g fumaric acid in 15 ml ethanol is added slowly. The mixture is allowed to stand over night. The precipitate is isolated by suction, washed with ethanol and dried. 10.2 g of neutral fumarate are thus recovered. Its melting point is 170° C. recrystallisation from 50 ml ethanol gives 6.1 g of an analytical sample whose melting point remains unaltered.

EXAMPLE II 2-(dicyclopropylmethylamino) thiazoline and its neutral fumarate

Step a. N-(1,1 decyclopropylmethyl) N'-($\beta$-chloroethyl) thiourea 9.2 g of $\beta$-chloroethyl isothiocyanate dissolved in 20 ml tetrahydrofuran are added dropwise to a solution of 9 g of dicyclopropylmethylamine in 70 ml tetrahydrofuran. The reaction mixture is kept at a temperature of from 0° to +5° C during the addition, then maintained at room temperature for 2 hours. The solvent is evaporated to dryness and the residue, consisting essentially of N-(1,1-dicyclopropylmethyl) N'-($\beta$-chloroethyl) thiourea, is recovered and used without any further purification for the next step of the synthesis.

Step b. 2-(dicyclopropylmethylamino) thiazoline

The raw N-(1,1-dicyclopropylmethyl) N'-($\beta$-chloroethyl) thiourea obtained by step a) is suspended in 100 ml of water and dissolved by warming. After complete solution, the aqueous phase is extracted with ether; the organic phase is discarded. The aqueous solution is made alkaline by adding an excess of 30% soda. An oily fraction separates which is then extracted with ether. The organic solution is washed with water, dried on sodium sulphate, filtered and evaporated to dryness. The cristallized residue is purified by dissolving it in the minimum amount of hot cyclohexane. By standing the solution in a cool place, 6 g of 2-(dicyclopropylmethylamino) thiazoline melting at 127°–128° C (with decomposition) are recovered.

Step c. 2-(dicyclopropylmethylamino) thiazoline, neutral fumarate 6.1 g of 2-(dicyclopropylmethylamino) thiazoline are dissolved in 20 ml ethanol. 1.8 g of fumaric acid dissolved in 20 ml ethanol are then added. The mixture is stirred for 2 hours. The precipitate of the fumarate is separated by suction, washed with ethanol and dried. 7.2 g of 2-(dicyclopropylmethylamino) thiazoline fumarate are thus recovered, which may be further purified by recristallisation from ethanol. 6.5 g of purified fumarate melting at 195° C are obtained.

EXAMPLE III 2-(1'-cyclopropylethylamino) oxazoline and its acid fumarate

Using the procedure described in Example I step a), starting from 6 g of 1-cyclopropylethylamine and 7.5 g of $\beta$-chloroethyl isocyanate, 12.5 g of N-(1'-cyclopropylethyl) N'-($\beta$-chloroethyl) urea melting at 85°–86° C are obtained.

The latter is cyclised using the procedure of Example I step b) and gives 2-(1'-cyclopropylethylamino) oxazoline. Its melting point is about 35°–41° C and its boiling point Eb 0.5 : 86°–87° C.

By adding an ethanolic solution of fumaric acid, acid fumarate is formed which is then purified by recrystallisation from acetonitrile.

EXAMPLE IV 2-(1',1'-dicyclopropylmethylamino) imidazoline 6.8 g of dicyclopropylmethylamine are dissolved in 30 ml of dimethylformamide. 14.7 g of 2-methylthioimidazoline (hydroiodide) are added to this solution and the reaction mixture heated at 100° C during the course of 8 hours under an inert atmosphere. After allowing the reaction mixture to return to ambient temperature, dimethylformamide is distilled off and the residue is recrystallized from 25 ml ethyl acetate. 6.7 g of 2-(1',1'-dicyclopropylmethylamino) imidazoline (hydroiodide) melting at 149°–152° C with decomposition are recovered.

The hydroidide is converted into the free base by alkalinisation. The 2-(1', 1'-dicyclopropylmethylamino) imidazoline melts at 165° C.

EXAMPLE V

Using the procedures given in Example I, the following compounds are obtained:

Step c. N-[1-methylcyclopropyl-1) ethyl] N'-($\beta$-chloroethyl) urea

Using the procedure of step a) from Example I N-[1-(1-methylcyclopropyl-1) ethyl] N'-($\beta$-chloroethyl) urea is obtained and used without further purification for the next step.

Step d. 2[1-(1-methylcyclopropyl-1) ethylamino] oxazoline

Using the procedure of step b) from Example I, starting from the urea of the preceding step 2-[1(1-methyl cyclopropyl-1) ethylamino] oxazoline is recovered with a yield of 60%.

16.8 g of 2-[1-(1-methylcyclopropyl-1) ethylamino] oxazoline are dissolved in 100 ml hydrochloric acid N and after having distillated off the solvent, its hydro-

| DEFINITIONS OF THE SUBSTITUENTS | MELTING POINT OF THE INTERMEDIATE UREA | CHARACTERISTICS OF THE OXAZOLINE | MELTING POINT OF THE SALT OF THE OXAZOLINE |
|---|---|---|---|
| $R_1$ $R_2$ A n | | | |
| cyclo H O 1 propyl | 85° C | Eb 0,1 = 127–128° C | Fumarate F = 180° C |
| H H O zero | 125° C (dec) | Eb 0,05 = 75–80° C F = 44–46° C | |

EXAMPLE VI

2-[1-(1-methylcyclopropyl-1) ethylamino] oxazoline

Step a. 1-methyl 1-(2-oximidoethyl) cyclopropane

A mixture from 49 g (1-methylcyclopropyl-1) methyl ketone, 175 ml pyridine and 32 g hydroxylamine hydrochloride is heated on a water bath for 3 hours. After return to room temperature, the clear solution is distilled off under reduced pressure. The oily residue is then poured in 100 ml water and kept under stirring for one hour. The crystalls are filtered, washed with water and dried in an oven —47.8 g 1-methyl 1-(2-oximidoethyl) cyclopropane are thus recovered. After recrystallisation from heptane the pure product melts at 79°–80° C (with sublimation). The yield amounts 85%.

Step b. 1-(1-methyl cyclopropyl-1) ethylamine 45 g of 1-methyl 1-(2-oximidoethyl) cyclopropane are suspended in 170 ml tetrahydrofuran with strong stirring. After few minutes, the dissolution is complete and to the clear solution 44.5 g aluminium lithium hydride in suspension into a mixture of ether and tetrahydrofuran are added.

The whole is heated to reflux for 3 hours then let to return to room temperature. Afterwards, the excess of reagent is cautiously destroyed by adding water then dilute hydrochloric acid until acidic reaction. The acidic solution is then made strongly basic by adding potash and extracted many times with ether. The organic phases are united, washed with water, with a solution of sodium carbonate then with water, dried on sodium sulphate and distillated off until dryness.

42 g of raw product is thus recovered i.e. a yield of 76%. The raw 1-(1-methylcyclopropyl-1) ethylamine is at once purified by fractionnated distillation then converted into its hydrochloride by dissolution in ether saturated with hydrochloric acid gas. After cooling the hydrochloride crystalizes. It is further purified by recrystallisation from acetonitrile. It melts at 215° (with dec.)

The hydrochloride is further converted into its free base with a yield of 71%. The (1-methylcyclopropyl-1) ethylamine boils under atmospheric pressure at 108°–110°. $n_D^{23}$ = 1,4310.

chloric is recovered.

The 2-[1-(1-methylcyclopropyl-1) ethylamino] oxazoline occurs as white crystalls, soluble in water, giving a basic solution.

EXAMPLE VII

2-[bis(2-methylcyclopropyl-1)methylamino] oxazoline, trans - trans isomers.

Using the procedure of Example VI, starting from di-(2-methylcyclopropyl-1) ketone trans-trans isomers obtained according to Hanack Chem Ber 96 (1963) 1259, the following compounds were obtained:

oxime of di-(2-methylcyclopropyl-1) ketone ($Eb_{15}$ = 120° – 126° $n_D^{23}$ = 1,4946)

bis-(2-methylcyclopropyl-1) methylamine ($Eb_{13}$ = 58°–60°)

raw N-[bis-(2-methylcyclopropyl-1)methyl] N'-($\beta$-chloroethyl) urea

2-[bis-(2-methylycyclopropyl-1) methylamino] oxazoline melting at 75°–77° after recrystallisation from heptane.

The oxazoline dissolved in the stoechiometric amount of hydrochloric acid is converted into its hydrochloride which is recovered after distillation to dryness.

EXAMPLE VIII

2-[1-(1-butylcyclopropyl-1) ethylamino] oxazoline

Using the procedure of example VI and starting from (1-butylclopropyl-1) methylketone, the following compounds are produced:

1-butyl (2-oximidoethyl) cyclopropane ($Eb_{13}$ = 115°–118° $n_D^{24}$ = 1,4672)

1-(1-butylcyclopropyl - 1) ethylamine [Eb 65°–66° $n_D^{21}$ = 1,4465 - hydrochloride F = 181–182 (subl.)]

N-(1-butyl cyclopropyl-1 1'-ethyl N'-($\beta$-chloroethyl) urea M.P = 74°–76°.

2[1-(butylcyclopropyl-1) ethylamino] oxazoline melting at 51°–53°.

The compound is purified by distillation under reduced pressure ($Eb_{0.05} = 82°-83°$). It is converted into the hydrochloric acid addition salt by means of the stoechiometric amount of hydrochloric acid and evaporation of the solvent to dryness.

EXAMPLE IX

2-[(1-cyclopropyl-1) 2-methylpropylamino] oxazoline and its hydrochlroride.

Using the procedure of Example VI and starting from (cyclopropyl-1) 2-methylpropyl ketone, the following compounds are obtained:

(1-cyclopropyl-1) 1-oximido 2-methylpropane melting at 68°–69°

(1-cyclopropyl-1) 1-amino 2-methylpropane boiling at 132°–135° under atmospheric pressure (hydrochloride M.P = 260° (dec.)

raw N-[1-(1-cyclopropyl-1) 2-methylpropyl] N'-($\beta$-chloroethyl) urea

2-[(1-cyclopropyl-1) 2-methylpropylamino] oxazoline melting at 92.5°–93° (dec.).

Its hydrochloride is obtained after solution into the stoechiometric amount of hydrochloric acid.

The starting material, (cyclopropyl-1) 2-methylpropylketone is obtained according to the process of Fauvarque Bull. Soc. Chim. France 161 (1969).

EXAMPLE X

2-[1'-(2,2-dimethylcyclopropyl-1) ethylamino] oxazoline and its hydrochloride Using the procedure disclosed in Example VI and starting from (2,2-dimethylcyclopropyl-1) methyl ketone prepared according to M. Julia Bull. Soc. Chim. France 1708 (1960), the following compounds are obtained:

2-(2,2-dimethylcyclopropyl-1) 2-oximidoethane ($Eb_{0.5} = 90°-91°$. $n_D^{24} = 1.4640$)

1-(2,2-dimethylcyclopropyl-1) ethylamine $Eb_{760} = 124°-125°$ $n_D^{23} = 1.4310$ hydrochloride MP = 205°–207°

N-[1-(2.2-dimethylcyclopropyl-1) ethyl] N'-($\beta$-chloroethyl) urea MP = 112°–113°

2-[1'-(2.2-dimethylcyclopropyl-1) ethylamino] oxazoline melting at 97°–98°

Its hydrochloride is obtained according to the above described procedure.

EXAMPLE XI

2-(N-dicyclopropylmethyl N-ethyl) amino oxazoline and its acid fumarate

Step a. N-ethyldicyclopropylmethylamine 4 g dicyclopropylmethylamine are dissolved in 30 ml tetrahydrofuran. To this solution, one adds dropwise a solution of 1.60 g acetaldehyde in 10 ml ethanol. The reaction mixture is kept under stirring for 30 minutes; then the precipitate of Schiff base is separated, washed many times with water and dried under vacuum.

The raw Schiff base is further redissolved in 40 ml methanol and a 5% solution of sodium borohydride in methanol — water is added — After completion of this addition, the mixture is heated to reflux for 15 minutes, then placed in a cooled place until return to about 20° C. 30 ml iced water are then added and the mixture is stirred for 30 mn. The precipitate is separated by decanting it and taken up in 20 ml isopropyl ether. The organic solution is washed with water, discoloured with activated charcoal, filtered and dried. The solvent is further evaporated off under reduced pressure.

4.97 g N-ethyldicyclopropylethylamine are thus obtained ($Eb_{64} = 74°-86°$). The raw amine is purified by converting it into its hydrochloride melting at 156°–159° (sublim.) after recrystallisation from ethanol Step b. [N-(dicyclopropylmethyl) N-ethyl] N'-($\beta$-chloroethyl) urea Using the same procedure as at step a) of Example I [N-(dicyclopropylmethyl) N-ethyl] N'-($\beta$-chloroethyl) urea is obtained with an about quantitative yield. It is used without further purification for the next step of the synthesis.

step c. 2-[N-(dicyclopropylmethyl) N-ethylamino] oxazoline and its fumarate

Using the same procedure as in step b) of Example I 2-[N-(dicyclopropylmethyl) N-ethylamino] oxazoline is obtained as a liquid, boiling at 70°–71° under a pressure of 0.05 mm.

After solution in ether and addition of an ethanolic solution of fumaric acid, crystals of acid fumarate are isolated and purified.

It occurs as white crystals, very soluble in water, melting at 130° (dec.)

EXAMPLE XII

2-[N-(dicyclopropylmethyl) N-isobutylamino] oxazoline and its acid fumarate

Operating as in Example XI and starting from dicyclopropylmethylamine and isobutyraldehyde, the following compounds are obtained:

(dicyclopropylmethyl) isobutylamine ($Eb_{16} = 87°-88°$)

[N-(dicyclopropylmethyl) isobutyl] N'-($\beta$-chloroethyl) urea

2-[(dicyclopropylmethyl) isobutylamino] oxazoline ($Eb_{0.05} = 83°-85°$)

and its acid fumarate melting at 125° after recrystallisation from acetonitrile.

EXAMPLE XIII

2-(1-cyclopropyl 1-tert-butyl methylamino) oxazoline and its hydrochloride

Using the same procedure as in Example VI and starting from cyclopropyl tert-butyl ketone the following compounds are produced:

oxime of cyclopropyl tert-butyl ketone MP = 110°–112° cyclopropyl tert-butyl methylamine ($Eb = 142°-148°$ $n_D^{26} = 1.4232$)

N-(cyclopropyl tert-butylmethyl) N'-($\beta$-chloroethyl) urea 2-(cyclopropyl tert-butyl methylamino) oxazoline MP = 86°–87° after recrystallisation from heptane.

The hydrochloride is obtained by addition of the stoechiometric amount of hydrochloric acid.

The starting material, cyclopropyl tert-butyl ketone is obtained according to the process described by Fauvarque Bull. Soc. Chim. France 161 (1969).

EXAMPLE XIV

2-(dicyclopropylmethylamine) oxazoline

Step a. dicyclopropylmethyl phenylcarbamate

To a solution of 166.5 g dicyclopropylmethyl amine in 151.5 g of triethylamine and 1500 ml water, 234 g phenyl chloroformate are added dropwise under vigourous stirring. The reaction mixture is cooled in order that the inner temperature lies between +5° and +10° C. After completion of the addition which lasts about 30 minutes, the cooling is withdrawn and the reaction mixture let to revert to room temperature. After standing two hours at about 20° C the precipitate is separated by filtration, washed with water until the washings will be neutral, then dried in an oven — 307 g of dicyclopropylmethyl phenylcarbamate are thus recovered i.e. a yield of 88%. The compound melts at 90°–94°. For analytical purpose, a sample is recrystallised from water. It melts at 92°–94°.

Step b. N-(dicyclopropylmethyl) N'-(β-hydroxyethyl) urea

In a three-neck flack 100 g dicyclopropylmethyl phenylcarbamate, 39 g ethanol amine and 450 ml water are successively introduced. The mixture is heated to reflux for 2 hours. After return to room temperature, the aqueous solution is extracted twice with chloroform. The chloroformic washings are separated, washed with water, dried and filtered. The solvent is distilled off and the dry residue is pasted in 500 ml ether. The insoluble matter is recovered by filtration, pasted again with ether and dried.

67 g N-(dicyclopropylmethyl) N'-(β-hydroxyethyl) urea are thus obtained. The yield amounts 78%. The pure compound melts at 112°–114°.

Step c. 2-(dicyclopropylmethylamino) oxazoline 15.8 g of N-(dicyclopropylmethyl) N'-(β-hydroxyethyl) urea obtained in the preceding step are added to a solution of 6.4 ml thionyl chloride in 160 ml chloroform. The mixture is stirred for 30 mn while maintaining the inner temperature between +5° and +10° C. The solvent and excess of reagent are distilled off under vacuum at a temperature below 40°.

The dry residue consisting of raw N-(dicyclopropylmethyl) N'(β-chloroethyl) urea is suspended in 100 ml water and heated to reflux for 30 mn. After standing in a cool place, the mixture is extracted with 20 ml ether three times. The ethereous phases are discarded and the aqueous solution is made basic by adding 10 ml concentrated ammonia.

The oxazoline precipitates and is extracted with ether. The ethereous solution is washed with water, dried on sodium sulphate, filtered and evaporated to dryness.

9.3 g 2-(dicyclopropylmethylamino) oxazoline are thus obtained i.e. a yield of 64%.

After recrystallisation of an analytical sample from hexane the melting point of pure 2-(dicyclopropylmethylamino) oxazoline is 106°–107°.

The compound is identical with that obtained according to the procedure of Example I.

Using the preceding procedure but using 3-aminopropanol instead of ethanol-amine,2-(dicyclopropylmethylamino) dihydro m. oxazine is obtained after cyclisation. Its fumarate melts at 180°.

Similarly using 4-aminobutanol instead of ethanolamine, 2-(dicyclopropyl methylamino) 4, 5, 6, 7 - tetrahydro oxazine is obtained.

EXAMPLE XV

Pharmacological study of the compounds a. Acute toxicity

The acute toxicity has been determined on mice (strain CD) weighing between 20 and 22 g — by intraveinous, intraperitoneal and oral way with increasing dosis.

The compounds of formula I are of small toxicity. The average lethal dosis ranges from 100 500 mg/kg by intraperitoneal way and from 250 to 2000 mg/kg by oral way.

b. Activity on systemic hemodynamics

The compounds of formula I have been administered to groups of dogs by intraveinous way after they were anesthezised. It occurs after a very transient increase of the blood pressure, a significant decrease of the blood pressure which ranges from 12 mm to 30 mm at a dosis from 100 to 600 γ/kg.

The compounds of formula I possess strong bradycardizing properties. At a dosis as small as 100 γ/kg they reduce the heart rate of 50%.

The compounds of formula I have little effect on heart output. Only high dosis induce a significative decrease.

The compounds of formula have a long-lasting effect on the anesthezied dogs. A dosis as 300γ/kg decreases the blood pressure of said dogs for more than an hour.

What we claim is:

1. A pharmaceutical composition containing as active ingredient an amount effective to lower blood pressure of a compound selected from the group consisting of:
   a. cyclopropylmethylamine of the formula

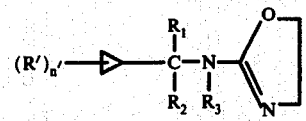

wherein $R_1$ and $R_2$, which are the same or different, each represent a hydrogen atom, a lower alkyl radical, a cyclopropyl radical or a cyclopropyl radical bearing one or more lower alkyl radicals, R' represents hydrogen or a lower alkyl radical, $R_3$ represents a hydrogen atom or a lower alkyl radical, and n' represents 0, 1, 2 or 3, and b. physiologically acceptable acid addition salts thereof of a mineral or organic acid, in admixture with a pharmaceutically acceptable non-toxic inert carrier suitable for oral, parenteral, sublingual, or rectal administration.

2. The pharmaceutical composition according to claim 1, in which the composition is in unit dosage form containing from 1.5 mg to 5 mg of said compound per unit dosage.

3. The pharmaceutical composition according to claim 2, in the form of tablets, ampules, capsules, drops, sublingual tablets, or suppositories.

4. The pharmaceutical composition according to claim 1, wherein the substituted cyclopropylmethylamine is 2-(dicyclopropylmethylamino) oxazoline.

5. The pharmaceutical composition according to claim 4, in which the composition is in unit dosage form containing from 1.5 mg to 5 mg of said compound per unit dosage.

6. The pharmaceutical composition according to claim 5, in the form of tablets, ampules, capsules, drops, sublingual tablets, or suppositories.

7. A method of lowering blood pressure, which consists in administering orally, parenterally, sublingually or rectally to a patient for the purpose of lowering the blood pressure of that patient, an amount which is safe and effective to lower blood pressure of a compound selected from the group consisting of:

a. cyclopropylmethylamine of the formula

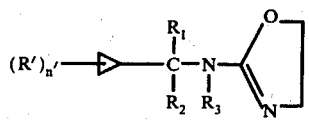

wherein $R_1$ and $R_2$, which are the same or different, each represent a hydrogen atom, a lower alkyl radical, a cyclopropyl radical or a cyclopropyl radical bearing one or more lower alkyl radicals, $R'$ represents hydrogen or a lower alkyl radical, $R_3$ represents a hydrogen atom or a lower alkyl radical, and $n'$ represents 0, 1, 2 or 3, and b. physiologically acceptable acid addition salts thereof of a mineral or organic acid.

8. The method of claim 7, wherein the safe but effective amount of said compound is from 3 mg to 15 mg daily.

9. The method according to claim 7, wherein the substituted cyclopropylmethylamine is 2-(dicyclopropylmethylamino) oxazoline.

10. The method of claim 9, wherein the safe but effective amount of said compound is from 3 mg to 15 mg daily.

* * * * *

UNITED STATES PATENT OFFICE
CERTIFICATE OF CORRECTION

Patent No. 3,988,464      Dated October 26, 1976

Inventor(s) Charles Malen, Monique Desnos, Michel Laubie, & Jean-Claude Poignant It is certified that error appears in the above-identified patent and that said Letters Patent are hereby corrected as shown below:

Col. 9, under heading of:
DEFINITIONS OF THE SUBSTITUENTS

| $R_1$ | $R_2$ | A | n |
|---|---|---|---|
| cyclo propyl | H | O | 1 |
| H | H | O | zero |

Page 11, Example V:
Please change to read as follows:

DEFINITIONS OF THE SUBSTITUENTS

| $R_1$ | $R_2$ | A | n |
|---|---|---|---|
| cyclopropyl | H | O | 1 |
| H | H | O | zero |

(Example XIV)
Col. 13, fourth line from bottom:

"tetrahydro oxazine"

(Example XIV) (Page 17, line 25)
Please change to read:

--- tetrahydrooxazepine ---

Signed and Sealed this

Sixth Day of December 1977

[SEAL]

Attest:

RUTH C. MASON
*Attesting Officer*

LUTRELLE F. PARKER
*Acting Commissioner of Patents and Trademarks*